US00PP08346P

United States Patent [19]

Nelson et al.

[11] Patent Number: Plant 8,346

[45] Date of Patent: Aug. 17, 1993

[54] STRAWBERRY PLANT NAMED 'PSI 308'

[75] Inventors: Michael D. Nelson, Davis; Steven D. Nelson, Watsonville; Daniel T. Schmida, Aptos, all of Calif.

[73] Assignees: Coast Cooling, Inc.; Plant Sciences, Inc., both of Watsonville, Calif.

[21] Appl. No.: 806,168

[22] Filed: Dec. 11, 1991

[51] Int. Cl.[5] ..... A01H 5/00

[52] U.S. Cl. ..... Plt./49

[58] Field of Search ..... Plt. 48, 49

*Primary Examiner*—James R. Feyrer

*Attorney, Agent, or Firm*—Christie, Parker & Hale

[57] ABSTRACT

A new variety of strawberry named 'PSI 308' which is capable of producing moderately high yields of relatively large, smooth textured symmetrical fruit. The fruit is exceptionally glossy, having good juiciness and flavor, with moderate firmness and holding quality. The variety is characterized by its erect growth habit and exceptionally long and erect primary peduncles which extend the inflorescence beyond the foliage during much of the season and by its relatively light colored canopy.

3 Drawing Sheets

BACKGROUND OF THE INVENTION

The new variety of strawberry was discovered as a seedling in a controlled breeding plot in Watsonville, Calif. The seedling was grown and asexually propagated by stolons during spring and summer seasons and after being selected, clones of the new variety were further asexually propagated and extensively tested over a two-year period. This propagation and testing has demonstrated that the combination of traits disclosed herein which characterize the new variety are fixed and retained true to type through successive generations of asexual reproduction.

SUMMARY OF THE INVENTION

The present invention relates to a new and distinct strawberry variety. The varietal denomination of the new variety is 'PSI 308', botanically known as *F. chiloensis* Duch. var. ananassa, and hereinafter referred to as '308. The following combination of characteristics distinguish the new variety:

1. short-day type fruiting habit;
2. vigorous, erect plant with relatively light colored canopy;
3. exceptionally long primary peduncles, extending inflorescence beyond foliage during much of the season; and
4. relatively large, smooth and symmetrical fruit having good flavor, excellent gloss and bright red color.

BRIEF DESCRIPTION OF THE ILLUSTRATIONS

The accompanying photographs show typical specimens of the new variety at various stages of development in color as nearly true as it is possible to make in color illustrations of this character.

Figure 1:
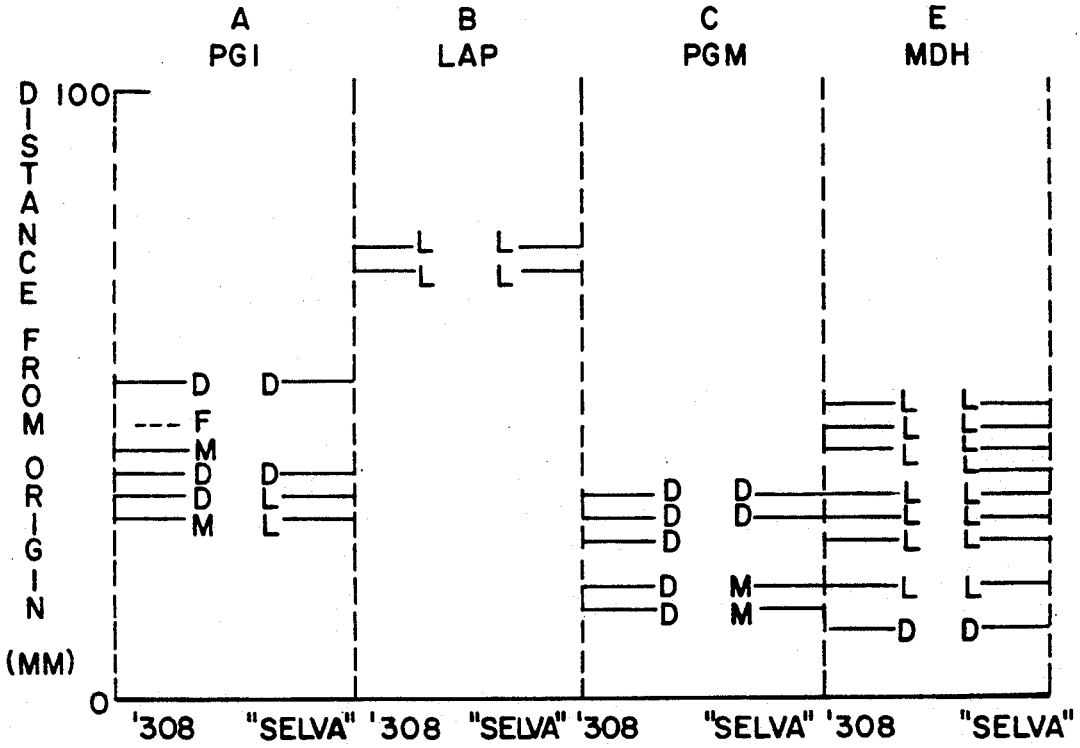

FIG. 1 shows the isozyme patterns comparing those of 'PSI 308' to those of the variety 'Selva'.

Figure 2:
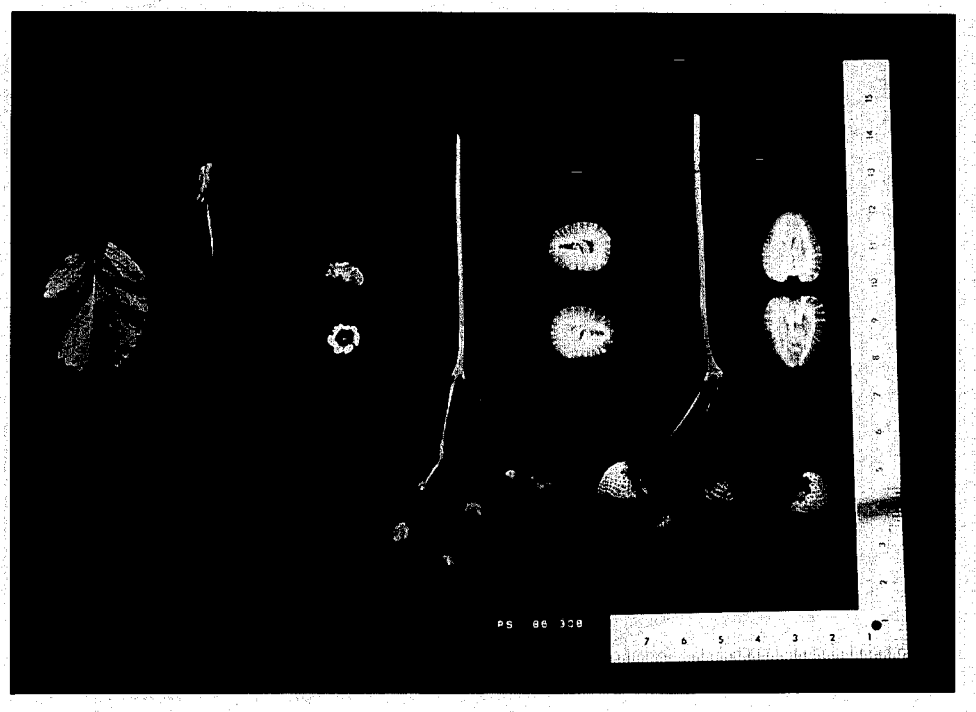

FIG. 2 is an illustration showing typical plant parts of the new variety including leaves (both the lower surface of a mature leaflet and the upper surfaces of a mature trifoliate leaf); the individual flowers; fruit positioning in clusters on peduncles and pedicels; and, mature fruit. Two fruit clusters are pictured, one with all fruit immature, and the other with the primary berry being mature and at harvest stage. Also shown are the cross-sectional and longitudinal views of mature fruit, illustrating typical light flesh, conspicuous core and core cavity.

Figure 3:
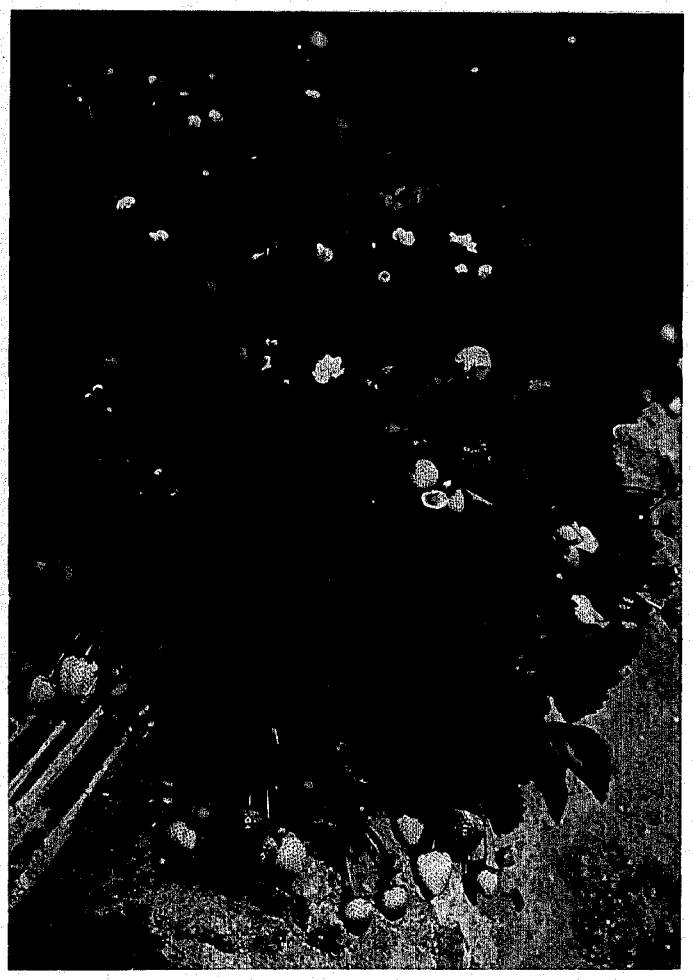

FIG. 3 is another illustration showing typical plant growth, flowering and fruiting characteristics in mid-June. The photograph illustrates the erect plant growth habit with relatively long and erect primary peduncles bearing infloresence. The flowering and fruiting habits are also shown with many flowers characteristically presented beyond the canopy formed by the foliage.

DESCRIPTION OF THE NEW VARIETY

The following is a detailed description of the new variety including fruit production, morphological, electrophoretic and pest reaction characteristics. '308 characteristics are compared to those of the central California coast commercial standard strawberry cultivar, 'Selva' (U.S. Plant Pat. No. 5,266) and 'PSI-S86.118' (U.S. Plant Pat. Ser. No. 07/635,220), hereinafter referred to as '118.

I. Fruit Production Characteristics

The new variety is primarily adapted to the climate and growing conditions of the central California coast, where it was selected and tested. This region provides the winter temperatures for it to produce a strong vigorous plant and remain in fruit production from April through September. The nearby Pacific ocean provides cool temperatures which maintain fruit quality during the summer production months.

Initial yield studies have shown that '308 is capable of producing moderately heavy season total yields, somewhat less than 'Selva' and '118, with a season average fruit size slightly larger than 'Selva' and considerably larger than '118. When planted in mid-November, the new variety begins to fruit in mid-April, peaks during the second and third weeks of June and produces fruit consistently through early September. '308 produces considerably less fruit than 'Selva' and '118 during the months of September and October.

II. Varietal Morphology and Electlrophoretic Description

The following detailed description of the new variety is based on observations taken in July from plants that were planted as dormant rootstock in mid-November in Wastsonville, Calif. The described characteristics of the new variety may vary slightly depending upon evaluation date and variations in environmental factors including weather (temperature, humidity and light intensity), day length, soil and location. '308 has not been observed under all possible environmental conditions. Color terminology is in accordance with the Munsell Book of Colors, Munsell Color, Baltimore, Md. (1976).

Parentage: '308 is a result of an open pollinated seedling of unknown parentage.

Fruit: '308 fruit characteristics are compared to those of 'Selva' and '118 in Table 1.

TABLE 1

Comparison of mid-summer 1991 fruit quality characteristics of '308, 'Selva' and '118 from fruit produced in Watsonville, California.

| Character | '308 | 'Selva' | '118 |
|---|---|---|---|
| MUNSELL SURFACE COLOR | NEAR 7.5R 3/12 | 7R 4/11* | NEAR 7.5 3/10 |
| 1° FRUIT SIZE L × W (CM) | 5.14 × 4.63 | 5.33 × 4.75 | 4.12 × 4.16 |
| CALYX DIAMETER (CM) - 1° FRUIT | 5.7 | 4.5 | 5.6 |

*Surface color according to Voth et al., U.S. Plant Pat. No. 7,172 ('Irvine') 1990.

Fruit is smooth and medium to long conic in shape, mostly symmetrical, with some long wedge shaped, particularly the larger primary fruit. The fruit surface is lighter in color than '118, and slightly darker red than 'Selva', with a light colored flesh. Primary fruit are large, comparable to 'Selva' and considerably larger than '118 as shown by the measurements. Fruit is less round than that of '118. '308 fruit is smoother than 'Selva', with very few sharp ridges or grooves. Achenes are typically positioned flush with the fruit surface, but can range from being slightly exerted to slightly sunken, unlike those of '118 (typically positioned exerted from fruit surface). The achenes are spaced evenly over the entire fruit surface with virtually no seedy tipped fruit produced. Fruit is more juicy and more glossy than 'Selva', comparable to '118, but not quite as flavorful as '118. Fruit is considered less firm and less durable in storage and shipping than the two comparative varieties. Calyx diameter of primary fruit is relatively large, comparable to that of '118, considerably larger than that of 'Selva', as shown by the measurements. '308 primary fruit average about 16 sepals per calyx, secondary fruit about 13.5 sepals per calyx. The calyx attaches firmly to slightly below the base of the fruit, rarely on a neck. Sepals are elliptical to narrow ovately shaped having acute apexes and few serrations, typically overlapping at the sepal base. '308 sepals have considerably fewer and shallower serrations compared to those of 'Selva'. Typically, the fruit have a conspicuous light colored core and core cavity. Fruit skin is considerably more susceptible to cracking due to rain than 'Selva'.

Plant: Plants grow vigorously in the fruiting field if exposed to proper chilling levels prior to being dug and, artifically, prior to being planted. The plants grow considerably slower than 'Selva' in the spring, but have unusually caught up by mid-June, eventually growing taller than 'Selva'. Foliage grows upright and becomes relatively dense, somewhat more upright and dense than 'Selva', not quite as dense as '118, consisting predominantly of three foliate leaves. The plant crown branches similarly to the comparative varieties, averaging about five crowns per plant by mid-July, and attaches to the soil slightly less firmly than 'Selva', more firmly than '118. The plant canopy has a relatively light colored appearance due to lighter colored foliage and greater inflorescence exposure than 'Selva' and '118.

Foliage: '308 foliage characteristics are compared to those of 'Selva' and '118 in Table 2.

TABLE 2

Comparison of mid-summer 1991 foliage characteristics of '308, 'Selva' and '118 from plants grown in Watsonville, California.

| CHARACTER | '308 | 'SELVA' | '118 |
|---|---|---|---|
| Munsell Leaf Color (Upper Surface) | Near 5 GY 4/6 | Near 7.5 GY 4/4 | Near 7.5 GY 3/4 |
| Petiole Length (CM) | 23.5 | 20.6 | 21.7 |
| Petiolule Length (MM) | 12.4 | 11.3 | 12.9 |
| Terminal Leaflet Size-L X W (CM) | 9.7 × 8.4 | 9.3 × 8.5 | 9.3 × 8.6 |
| Terminal Leaflet Ratio (L/W) | 1.15 | 1.09 | 1.08 |
| Terminal Leaflet Serration Depth (MM) | 4.4 | 4.9 | 6.6 |

Foliage is lighter green and more yellow than that of 'Selva' and '118. Petioles are slightly longer than those of 'Selva' and '118, while petiolules are slightly longer than those of 'Selva', yet slightly shorter than those of '118. Terminal leaflets are longer and narrower, less round and more oval shaped than those of 'Selva' and '118, as shown by the L×W leaflet measurements and the ratio of those measurements. Terminal leaflet serrations are slightly shallower than those of 'Selva', considerably shallower than those of '118, having moderately acute apexes with few overlapping. '308 leaves are not particularly glossy, similar to the comparative varieties. Leaf texture ranges from smooth flat to mildly corrugated. Bract leaves occur singly or in pairs on about two thirds of the petioles. Pubescence occurs irregularly perpendicular to petioles and irregularly parallel to upper and lower leaf surfaces.

Isozymes in leaf extract: Studies of protein polymorphism by the starch gel electrophoresis method were carried out to characterize the new variety and distinguish it from other varieties. Isozymes were extracted from young leaves and characterized using starch gel electrophoresis techniques. The following isozymes were characterized: phosphoglucoisomerase (PGI: EC 5.3.1.9), phosphoglucomutase (PGM: EC 2.7.5.1), leucine aminopeptidase (LAP: EC 3.4.11.1) and malate dehydrogenase (MDH: EC 1.1.1. 37). The plant material used was both field and green-house grown in Watsonville, Calif. Newly matured leaves (1 g fresh weight) were collected in the morning, held at 4°-8° C. and analyzed within 24 hours. Gel and electrode buffers for the enzyme systems analyzed are given in Table 3. Electrophoresis specifications for these enzyme systems are given in Table 4. The techniques and stains used were described in Arulsekar and Parfitt (1986) and Cousineau and Donnelly (1989).

TABLE 3

GEL AND ELECTRODE BUFFERS FOR FRAGARIA ENZYME SYSTEMS

| SYSTEM | GEL BUFFER | G/L | pH | BUFFER | G/L | pH |
|---|---|---|---|---|---|---|
| A | TRIS BASE | 6.5 | 8.3 | LITHIUM HYDROXIDE | 1.2 | 8.3 |
| | CITRIC ACID (MONOHYD.) | 1.5 | | | | |
| | | | | Boric Acid | 12.0 | |
| B | DL-HISTIDINE HCL (MONOHYD.) (MONOHYD.) | 1.2 | 7.0 | TRIS BASE | 16.5 | 7.0 |
| | | | | CITRIC ACID | 9.0 | |

TABLE 4

FRAGARIA ELECTROPHORESIS SPECIFICATIONS

| SYSTEM | ENZYME | pH | CURRENT | GEL SLICE |
|---|---|---|---|---|
| A | PGI | 8.3 | 275 V | 2 |
| A | LAP | 8.3 | 275 V | 4 |
| B | PGM | 7.0 | 150 V | 3 |
| B | MDH | 7.0 | 150 V | 2 |

Following electrophoresis, the gel was sliced into three slices and stained for each enzyme system. Banding patterns were interpreted as they developed and gel slices were fixed in 50% glycerol. The isozyme banding patterns for the four enzyme systems compared to those of 'Selva' are given in FIG. 1. The banding pattern codes referred to are those of Bringhurst et al. (1981) and plant patent application Ser. No. 07/635,220 (patent pending) describing PGI(A7) for strawberry variety '118. '308 has a pattern which separates it from all University of California patented varieties based on pattern A7 for PGI. This pattern differs from A4 in that the bottom band is very faint in A4, whereas in A7 the bottom three bands are moderate to dark.

Inflorescence: '308 inflorescence characteristics are compared to those of 'Selva' and '118 in Table 5.

TABLE 5

Comparison of mid-summer 1991 inflorescence characteristics of '308, 'Selva' and '118 from plants grown in Watsonville, California.

| CHARACTER | '308 | 'SELVA' | '118 |
|---|---|---|---|
| 1°Peduncle Length (CM) | 22.0 | 15.1 | 20.6 |
| 2° Peduncle Length (CM) | 2.8 | 3.0 | 2.6 |
| Length of Pedicel Bearing 1° Berry | 7.6 | 10.0 | 5.9 |

Inflorescence are borne on relatively long, thick and erect primary peduncles which extend the flowers and maturing fruit beyond the foliage during much of the season. The inflorescence remain upright until the weight of ripening fruit cause them to fall to the sides of the bed. Primary peduncles are slightly longer than those of '118, considerably longer than those of 'Selva'. Above the primary peduncle apex, the '308 inflorescence typically branches to form two to three secondary peduncles and a solitary pedicel bearing the primary berry. The secondary peduncles are slightly longer than those of '118, but slightly shorter than that of 'Selva'. The pedicel bearing the primary berry is longer than that of '118, but considerably shorter than that of 'Selva'. This pedicel typically originates singly from the primary peduncle apex, at the axil of secondary peduncles, and less frequently from one of these secondary peduncles. Secondary and tertiary berries are typically borne on pedicles arising from secondary peduncle apexes. Flowers are moderately large, readily seen above the plant canopy during much of the season. Flowers consist of about six (secondary flower) to eight (primary flower) obovate shaped petals. A single bract leaf, ranging in shape from elliptical to ovate, typically originates on a short petiole which arises from the primary peduncle apex, alongside the base of the secondary peduncles. The largest inflorescence may also have a bract leaf at the apex of secondary peduncles, at the base of tertiary peduncles. Bracts typically originate at the apex of all peduncles, including primary, secondary and tertiary (when present) peduncles. Pubescence originates on all peduncles and pedicels, growing irregularly perpendicular to these surfaces.

Stolon production: Stolon production of '308 at the nursery level is better than that of '118, nearly as good as that of 'Selva'.

III. Pest Reactions

The new variety may not be resistant to any of the known insect and disease pests common in California. It is known to be moderately susceptible to the two-spotted spider mite, aphid and flower thrips. High concentration of flower thrips results in fruit discoloration and loss of sheen due to their destructive feeding habits on developing flowers and fruit. '308 is known to be moderately susceptible to powdery mildew, bacterial leaf spot and grey fruit mold. Laboratory and greenhouse studies have shown that '308 is susceptible to crown and root rot diseases caused by *P. cactorum* and *C. acutatum*.

We claim:

1. A new and distinct strawberry variety substantially as shown and described.

* * * * *

FIGURE I

'308 ISOZYME PATTERNS COMPARED TO SELVA

'308: A7 B3 C4 E1

"SELVA": A2 B3 C2 E2

D = DARK BAND

M = MODERATE-DARK BAND

L = LIGHT BAND

F = FAINT BAND

UNITED STATES PATENT AND TRADEMARK OFFICE

CERTIFICATE OF CORRECTION

PATENT NO. : Plant 8,346

DATED : August 17, 1993

INVENTOR(S) : Michael D. Nelson; Steven D. Nelson; Daniel T. Schmida

It is certified that error appears in the above-indentified patent and that said Letters Patent is hereby corrected as shown below:

Column 2, line 2, after "light" insert -- colored --.
Column 2, line 8, change "infloresence" to -- inflorescence --.
Column 2, line 15, change "'308" to -- '308 --.

Column 3, line 64, change "unusually" to -- usually --.
Column 3, line 68, change "'118" to -- '118 --.

Signed and Sealed this

Fifth Day of July, 1994

Attest:

Bruce Lehman

BRUCE LEHMAN

Attesting Officer

Commissioner of Patents and Trademarks